United States Patent
Zini et al.

(10) Patent No.: US 8,948,914 B2
(45) Date of Patent: Feb. 3, 2015

(54) SYSTEM AND METHOD FOR SECURELY TRANSPORTING AN ITEM

(75) Inventors: Aldo Zini, Venetia, PA (US); Barry Mark Skirble, Allison Park, PA (US); Peter T. Seiff, Gibsonia, PA (US); Kevin F. Seip, Richboro, PA (US)

(73) Assignee: Aethon, Inc., Pittsburgh, PA (US)

( * ) Notice: Subject to any disclaimer, the term of this patent is extended or adjusted under 35 U.S.C. 154(b) by 406 days.

(21) Appl. No.: 12/632,319

(22) Filed: Dec. 7, 2009

(65) Prior Publication Data

US 2010/0234995 A1 Sep. 16, 2010

Related U.S. Application Data

(60) Provisional application No. 61/120,290, filed on Dec. 5, 2008.

(51) Int. Cl.
*G05B 19/00* (2006.01)
*G05B 19/418* (2006.01)
*G06F 19/00* (2011.01)

(52) U.S. Cl.
CPC ...... *G05B 19/41895* (2013.01); *G06F 19/3462* (2013.01); *G05B 2219/31006* (2013.01); *G05B 2219/31086* (2013.01); *G05B 2219/31286* (2013.01); *G05B 2219/31432* (2013.01); *G05B 2219/31446* (2013.01); *G05B 2219/31454* (2013.01)
USPC .......................................... 700/258; 700/236

(58) Field of Classification Search
CPC ............... G05B 19/41895; G05B 2219/31286; G05B 2219/31432; G06F 19/3462
USPC .......... 414/281, 283; 700/245, 248, 236, 237, 700/258, 259; 901/1; 318/568.1, 568.11
See application file for complete search history.

(56) References Cited

U.S. PATENT DOCUMENTS

| | | | | |
|---|---|---|---|---|
| 5,314,243 A | * | 5/1994 | McDonald et al. | 312/215 |
| 6,325,586 B1 | * | 12/2001 | Loy | 414/281 |
| 6,339,732 B1 | * | 1/2002 | Phoon et al. | 700/237 |
| 6,543,983 B1 | * | 4/2003 | Felder et al. | 414/402 |
| 6,707,381 B1 | * | 3/2004 | Maloney | 340/568.1 |
| 6,935,560 B2 | * | 8/2005 | Andreasson et al. | 235/385 |
| 7,100,725 B2 | * | 9/2006 | Thorne | 180/169 |

(Continued)

FOREIGN PATENT DOCUMENTS

JP 2003000684 A * 1/2003 ............... A61J 3/00
WO WO 2007058048 A1 * 5/2007

OTHER PUBLICATIONS

Google Machine Translation of WO 2007-058048 (original PCT document published May 24, 2007).*

(Continued)

*Primary Examiner* — Behrang Badii
*Assistant Examiner* — David Testardi
(74) *Attorney, Agent, or Firm* — Buchanan Ingersoll & Rooney PC (57) ABSTRACT

A system. The system includes an apparatus and a server. The apparatus is configured for securely transporting an item from a first location to a second location, and includes a mobile robot and a cart. The cart is coupled to the mobile robot and includes at least one secure storage area. The server is communicably connected to the apparatus and includes a module. The module is configured to maintain a chain of custody record for the item.

16 Claims, 5 Drawing Sheets

(56) References Cited

U.S. PATENT DOCUMENTS

| | | | |
|---|---|---|---|
| 7,175,081 B2* | 2/2007 | Andreasson et al. | 235/385 |
| 7,212,098 B1* | 5/2007 | Trent et al. | 340/5.3 |
| 7,258,276 B2* | 8/2007 | Linton et al. | 235/385 |
| 7,262,698 B1* | 8/2007 | Frederick et al. | 340/545.6 |
| 7,336,174 B1* | 2/2008 | Maloney | 340/572.1 |
| 7,348,884 B2* | 3/2008 | Higham | 340/572.1 |
| 7,518,516 B2* | 4/2009 | Azevedo et al. | 340/572.1 |
| 7,630,791 B2* | 12/2009 | Nguyen et al. | 700/242 |
| 7,654,261 B1* | 2/2010 | Rockhold | 128/204.18 |
| 7,661,591 B2* | 2/2010 | Dearing et al. | 235/385 |
| 7,689,318 B2* | 3/2010 | Draper | 700/236 |
| 7,809,470 B2* | 10/2010 | Shoenfeld | 700/243 |
| 8,068,023 B2* | 11/2011 | Dulin et al. | 340/539.13 |
| 8,126,811 B2* | 2/2012 | Dolivo et al. | 705/51 |
| 8,224,664 B1* | 7/2012 | Louie et al. | 705/2 |
| 8,234,185 B2* | 7/2012 | Davis | 705/28 |
| 8,239,062 B2* | 8/2012 | Vahlberg et al. | 700/236 |
| 2003/0225596 A1* | 12/2003 | Richardson et al. | 705/2 |
| 2006/0079994 A1* | 4/2006 | Chu et al. | 700/231 |
| 2007/0129849 A1* | 6/2007 | Zini et al. | 700/258 |
| 2007/0228680 A1* | 10/2007 | Reppert et al. | 280/47.35 |
| 2008/0066207 A1* | 3/2008 | Beniyama et al. | 901/1 |
| 2008/0316045 A1* | 12/2008 | Sriharto et al. | 340/825.49 |
| 2009/0037020 A1* | 2/2009 | Brown | 700/240 |
| 2009/0091453 A1* | 4/2009 | Ishida et al. | 340/572.1 |
| 2009/0108016 A1* | 4/2009 | Brown et al. | 221/28 |
| 2009/0138122 A1* | 5/2009 | Wagner | 700/226 |
| 2009/0160646 A1* | 6/2009 | Mackenzie et al. | 340/572.1 |

OTHER PUBLICATIONS

Summerfield, Marc R., "Using the TUG self-guided robot to improve medication delivery cycle time (Product Spotlight)", Pharmacy Purchasing & Products (magazine), Dec. 2004, vol. 1 No. 4, p. 22.*

FirstHealth of the Carolinas newsroom article entitled, "Transport robots assist with flow of medication deliveries at FirstHealth Moore Regional", Mar. 2006, retrieved from http://www.firsthealth.org/About%20Firsthealth/Newsroom/2006/March/Transport%20robots%20assist%20with%20flow%20of%20medication%20deliveries%20at%20MRH.asp.*

LifeBridge Health Blogs article from Sinai Hospital entitled, "Pharmacy Robots Debut at Sinai", Nov. 5, 2008, downloaded from http://www.lifebridgeblogs.org/2008/11/05/pharmacy-robots-debut-at-sinai/.*

Noble, Suzanne, "As in Todays World, Security Takes Many Forms", Healthcare Purchasing News Online, May 2002, Cover Story, downloaded from http://www.hpnonline.com/inside/2002-05/0502cover.html.*

Pharmacy Purchasing & Products (magazine), "Medication Carts Buyer's Guide", vol. 3 No. 4, (Jun. 2006), pp. 12, 14, 16, 18, downloaded from http://www.pppmag.com/documents/V3N4/v3N4p12-18cartsbuyers.pdf.*

Pharmacy Purchasing & Products (magazine), Automated Dispensing Cabinets Buyer's Guide, vol. 3 No. 6, Sep. 2006, downloaded from http://www.pppmag.com/article/15/September_2006/Buyers_Guide_Automated_Dispensing_Cabinets/.*

* cited by examiner

SYSTEM AND METHOD FOR SECURELY TRANSPORTING AN ITEM

CROSS-REFERENCE TO RELATED APPLICATION

This application claims the benefit under 35 U.S.C. §119(e) of the earlier filing date of U.S. Provisional Patent Application No. 61/120,290 filed on Dec. 5, 2008.

BACKGROUND

This application discloses an invention which is related, generally and in various embodiments, to a system and method for securely transporting an item from a first location to a second location. The item may be transported within a variety of different environments. For purposes of simplicity, the invention will be described in the context of transporting items in a hospital facility.

Hospitals are required and or desire to track various items that are delivered internally from their internal service departments to various areas of the hospital, including but not limited to, nursing units, patients, ancillary and support areas, surgical and emergency areas, outpatient areas and clinics. Typical examples of this would be the delivery of medication to nursing units, the picking up of lab specimens from nursing areas, the delivery or pick up of blood products from the blood bank, food deliveries, supply deliveries and mail deliveries. Many of the deliveries may require tracking and security for regulatory purposes, such as the delivery and storage of controlled substances by the pharmacy or the delivery and storage of blood products from the blood bank. In other instances the tracking and security are highly desirable, such as the delivery of high cost or high alert (e.g., dangerous) medications.

Other than having a person deliver the item from a first location in the hospital to a second location in the hospital, hospitals currently do not have a reliable method for insuring a secure and traceable delivery of the item. For human delivery, a person from the delivering department must physically receive the item from a secure storage area within the department and complete the internal security compliance steps or receive the item from an outside entity, such as the US mail. The delivery person must then go to the area where the item has been requested and have the recipient acknowledge the delivery, almost always in writing.

The current human delivery or manual system is human resource intense, untimely, lacks security and where it is not required by law, is most often not employed. Instead, hospitals generally choose to use their human resources for pressing concerns.

Once an item has been delivered, it is either used or applied for patient care without delay or stored in a designated area for later use. The item may be stored in Automated Dispensing Cabinets (ADCs), refrigerators, locked or unlocked cabinets, open shelving or in designated rooms. In many instances, the current human delivery method has no system of feedback to be sure that once the item is received by an individual the item makes it to its proper destination for storage. Having the item reach the proper destination can be critical from a safety perspective as well as for product stability. For instance, an intravenous medication that has been prepared by the pharmacy may require refrigeration and is given an expiration date based on that storage condition. If the item is not stored properly the stability and potency of the medication is compromised and may render it ineffective or at least less effective than normal.

Some hospitals employ the use of pneumatic tube systems for the delivery of some items. In such instances, the item requiring delivery is placed in a plastic tube and sent through the system to the final destination. The final destination is generally known as a tube station, and the tube station typically includes an open bay to permit tubes to arrive. These open bays are unsecured and any person with access to the area may remove tubes or items without accountability. In most hospitals, pneumatic tube systems are not used for items requiring tracking and accountability, but that is not always the case.

In some hospital departments that frequently send items where security, tracking and accountability are required, there may exist an automated secure cabinet system. For example, such systems are sometimes employed by a pharmacy for the internal storage, dispensing and tracking of controlled substances. These systems may be electronically linked to ADCs located in areas external to the pharmacy area. However, these systems do not address delivery and therefore are employed in conjunction with the previous mentioned human delivery model.

For hospitals that utilize ADCs, the ADCs need to be routinely replenished. This replenishment is generally performed by human delivery, and although a centralized database may record the item's final disposition, the security, tracking and accountability of the delivery itself is not assured.

ADCs, also known as unit based cabinets, have become a standard part of the medication distribution system of many modern hospitals. The ADCs are stocked with various medications, and operate to dispense such medications to authorized personnel. In general, an individual ADC includes a computing device, an input device such as a keypad, a display device, and a plurality of normally locked drawers, where each drawer holds one or more types of medications. The computing device is in communication with the hospital network, and maintains a list of patients associated with the ADC.

In operation, the input device allows a person to enter information such as a user name and password. Once the user name and password are authenticated, a list of patients associated with the ADC may be displayed on the display device. The authorized person may then gain access to the medications needed for any of the patients on the list. For example, the authorized person may utilize the input device to select an individual patient from the displayed list of patients. Upon the selection of the individual patient, a list of medications and dosages for the selected patient may be displayed on the display device. The authorized person may then utilize the input device to select a particular medication of the selected patient. Upon the selection of the medication, the computing device may operate to initiate the unlocking and opening of the drawer which holds the selected medication. The authorized person may then remove the medication from the drawer for use with the selected patient. Upon the completion of this process, the drawer is closed and automatically locked. A similar sequence may then be utilized any number of times to gain access to additional medications for the selected patient or medications for other selected patients.

The ADCs are typically spread throughout the patient care areas in order to have the medication inventory closer to the actual point of use. Although the positioning of ADCs throughout the patient areas provides localized access to an inventory of medications, there are certain inefficiencies which result from the utilization of ADCs, particularly in the area of inventory maintenance. As various medications are dispensed from each of the ADCs, the ADCs communicate the reduction of the respective medication inventories to the hospital network so that the hospital pharmacy knows the medications and dosages which need to be replenished at each of the ADCs. On a periodic basis, the medication inventories held by the respective ADCs are replenished. The replenishment process typically involves having one or more persons manually transport medications from the hospital pharmacy to the individual ADCs. Such a process is labor intensive, prone to inaccuracies, and difficult to effectively manage.

SUMMARY

In one general respect, this application discloses a system. According to various embodiments, the system includes an apparatus and a server. The apparatus is configured for securely transporting an item from a first location to a second location, and includes a mobile robot and a cart. The cart is coupled to the mobile robot and includes at least one secure storage area. The server is communicably connected to the apparatus and includes a module. The module is configured to maintain a chain of custody record for the item.

In another general respect, this application discloses a method for securely transporting an item. According to various embodiments, the method includes identifying an item placed into a secured storage area of a cart, transmitting placement information regarding the identified item to a server, identifying when the item is removed from the secured storage area of the cart, and transmitting removal information regarding the identified item to the server.

Aspects of the invention may be implemented by a computing device and/or a computer program stored on a computer-readable medium. The computer-readable medium may comprise a disk, a device, and/or a propagated signal.

BRIEF DESCRIPTION OF THE DRAWINGS

Various embodiments of the invention are described herein in by way of example in conjunction with the following figures, wherein like reference characters designate the same or similar elements.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

Figure 1:
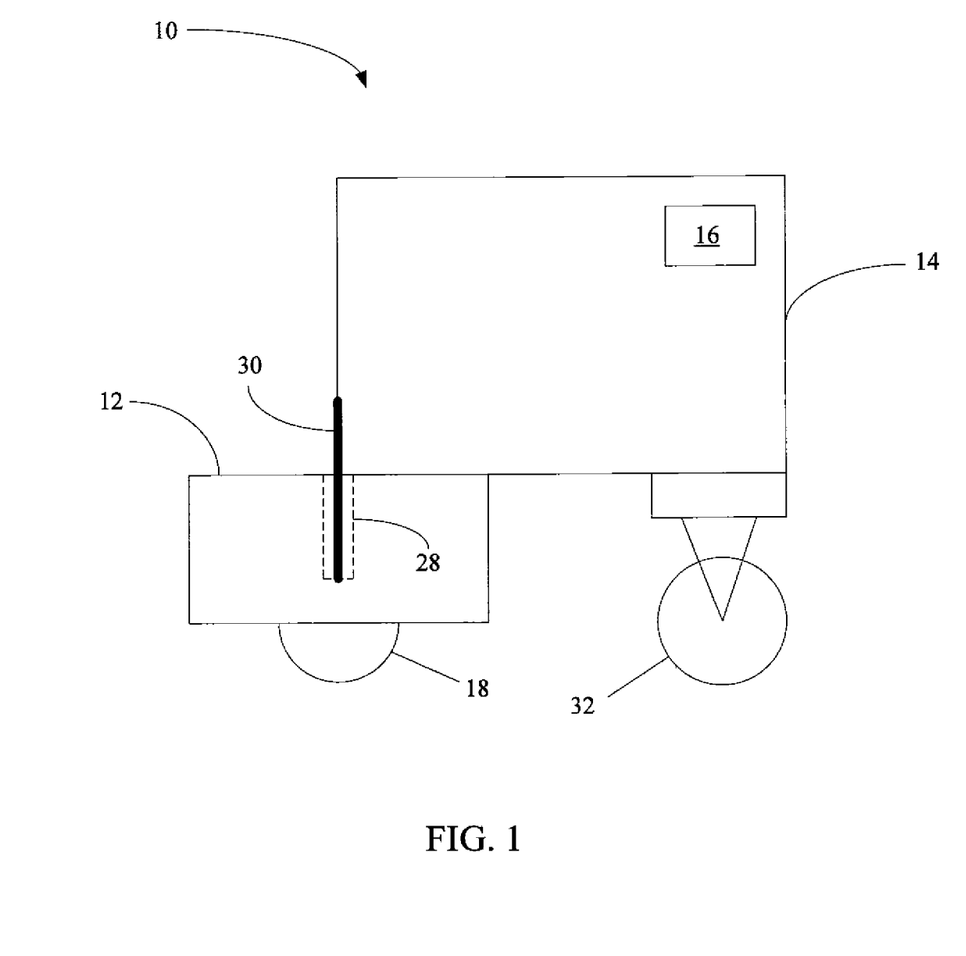
FIG. 1 illustrates various embodiments of an apparatus.

FIG. 1 illustrates various embodiments of an apparatus 10. The apparatus 10 may be utilized to securely transport items throughout an environment. For example, the apparatus 10 may be utilized to securely transport medicines, lab specimens, blood products, food, general supplies, mail, etc. throughout a hospital. Although the apparatus 10 may be utilized to transport a variety of different items throughout a variety of different types of facilities, for purposes of simplicity, the apparatus 10 will be described in the context of transporting medicines throughout a hospital facility. According to various embodiments, the apparatus 10 includes a mobile robot 12, and a cart 14 coupled to the mobile robot 12. The apparatus 10 may also include an interface 16 connected to the cart 12.

Figure 2:
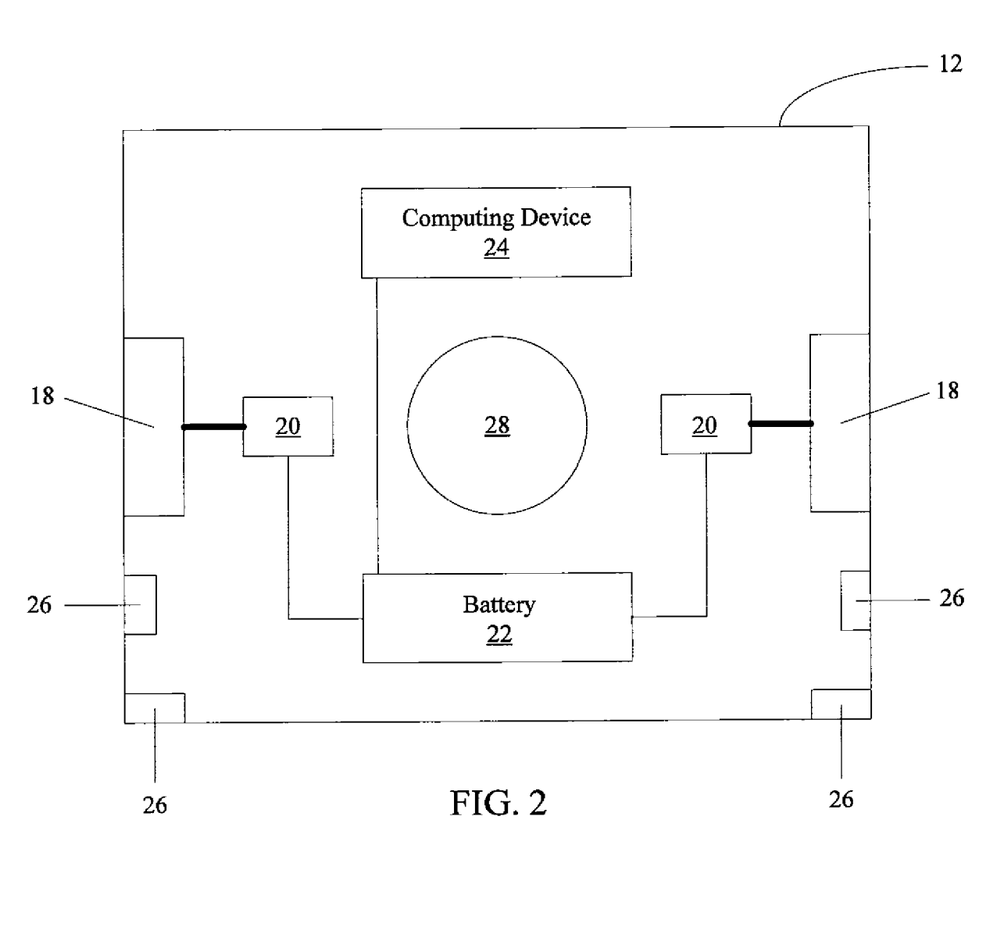
FIG. 2 illustrates various embodiment of a mobile robot of the apparatus of FIG. 1.

The robot 12 may be any suitable type of mobile robot. For example, according to various embodiments, the robot 12 may be configured similar to the robot described in U.S. Pat. Nos. 6,046,565 and 7,100,725, the contents of which are hereby incorporated. As shown in FIG. 2, according to various embodiments, the mobile robot 12 includes first and second wheels 18, first and second motors 20 mechanically coupled to the respective first and second wheels 18, a battery 22 electrically connected to the first and second motors 20, a computing device 24 connected to the battery 22, and a plurality of sensors 26 coupled to the computing device 24. For purposes of clarity, the electrical connections between the respective sensors 26 and the computing device 24 are not shown in FIG. 2. According to various embodiments, the mobile robot 12 also includes a receptacle 28 configured for receiving a post 30 (see FIG. 1) which couples the mobile robot 12 and the cart 14 to one another. The receptacle 28 may be configured to mechanically and electrically couple the mobile robot 12 and the cart 14 to one another when the post 30 is received by the receptacle 28. Aspects of the mobile robot 12 may be implemented by the computing device 24 and/or a computer program stored on a computer-readable medium. The computer-readable medium may comprise a disk, a device, and/or a propagated signal.

Figure 3:
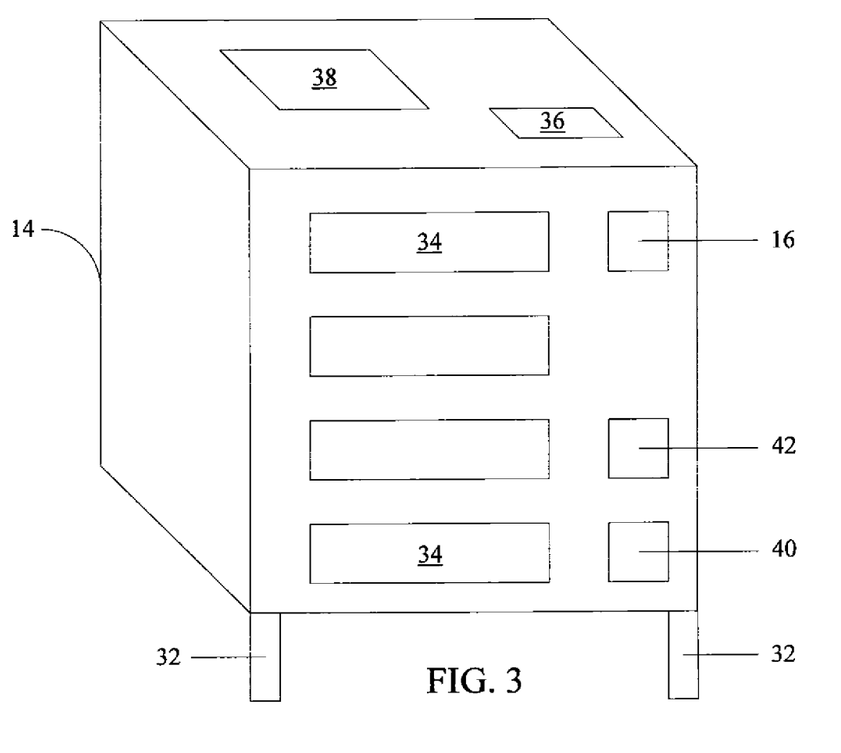
FIG. 3 illustrates various embodiments of a cart of the apparatus of FIG. 1.

The cart 14 may be any suitable type of cart utilized to securely transport items such as medicines, lab specimens, blood products, food, general supplies, mail, etc. throughout an environment. FIG. 3 illustrates various embodiments of the cart 14. The cart 14 includes first and second wheels 32, a plurality of storage areas 34, an input device 36 such as, for example, a keypad, a biometric reader, etc. and a passive radio frequency identification (RFID) tag reader 38. Although not shown in FIG. 3, the cart 14 may also include a battery and a computing device, or may utilize the battery 22 and the computing device 24 of the mobile robot 12. In general, one or more of the storage areas 34 are normally secured (e.g., closed and locked), and such secure storage areas 34 may hold one or more items to be delivered to throughout the facility. For example, the secure storage areas 34 may hold one or more medicines to be delivered to ADCs positioned throughout a hospital. At least some of the items may be packaged (e.g., medicines packaged in individual unit dose packages), and such packages may have RFID tags embedded therein. Alternatively, such packages may have one or more bar codes printed thereon. An authorized person may position a hospital issued passive radio frequency identification (RFID) tag proximate the passive tag reader 38 and/or use the input device 36 to enter a specific code, enter a biometric identification, etc. to cause one or more of the secure storage areas 34 to open, thereby gaining access to the items held by the secure storage areas 34. The apparatus 10 may transmit information regarding the position of the apparatus 10 within the facility, the person who gained access to the items, the time the person gained access to the items, etc.

According to various embodiments, the cart 14 also includes a second passive RFID tag reader 40. The second passive RFID tag reader 40 may be positioned at any number of suitable locations on or in the cart 14. When an item (e.g., a medication package) embedded with an RFID tag is removed from one of the secure storage areas 34 of the cart 14, the second passive RFID tag reader 40 is operative to identify the item as it is removed. The apparatus 10 may also transmit information regarding the removal of the item from the cart 14 such as, for example, the type of medication package removed, the time the medication package was removed, etc.

According to other embodiments, the cart 14 also includes a bar code reader 42. The bar code reader 42 may be positioned at any number of suitable locations on the cart 14. When an item (e.g., a medication package) having a bar code printed thereon is removed from one of the secure storage areas 34 of the cart 14, the person who removed the item may utilize the bar code reader to read the bar code on the removed item. The reading of the bar code is operative to identify the removed item. The apparatus 10 may also transmit information regarding the removal of the item from the cart 14 such as, for example, the type of medication package removed, the time the medication package was removed, etc.

As described in more detail hereinafter, the information transmitted from the apparatus 10, including the position of the apparatus 10 within the facility, the person who gained access to the secured items, the time the person gained access to the secured items, the type of item removed, the time item was removed, etc. may be utilized to establish a chain of custody record for the item.

The interface 16 is in communication with the computing device 24, and may be positioned at any number of locations in or on the cart 14. The interface 16 is configured to wirelessly communicate with at least one other automated device, and may be utilized to operate at least some of the functionality of the at least one other automated device. The other automated device may be embodied as, for example, an automated secure cabinet such as an ADC, an automated refrigeration unit, an automated bay of a tube station, etc. For some embodiments, when the apparatus 10 is proximate an ADC, the interface 16 may transmit an instruction to the ADC to display a list of medication packages which need to be replenished at the ADC. This automatic process eliminates the need for a hospital employee to advance through the user screens of the ADC to display the list. In addition, the interface 16 may receive the list from the ADC, and operate to unlock the secure storage area 34 which holds the first medication package on the list, thereby providing an authorized hospital employee access to the needed medication package. Furthermore, the interface 16 may transmit an instruction to unlock a drawer of the ADC based on the medication package which is removed from the cart 14.

According to other embodiments, the apparatus 10 includes the cart 14 and the interface 16, but not the mobile robot 12. In such embodiments, the cart 14 may be manually pushed or pulled from one location within the facility to another location within the facility, and the apparatus 10 retains all of the other functionalities described above. Therefore, the chain of custody record may also be established by this embodiment of the apparatus 10.

According to yet other embodiments, the apparatus 10 may include the cart 14, but not the mobile robot 12 or the interface 16. For such embodiments, the apparatus 10 may be utilized to deliver items (e.g., medications) to specific locations or to devices other than an ADC. In such embodiments, the cart 14 may be manually pushed or pulled from one location to another within the facility, and the apparatus 10 retains functionality for establishing a chain of custody for medications loaded onto or off of the cart 14.

Figure 4:
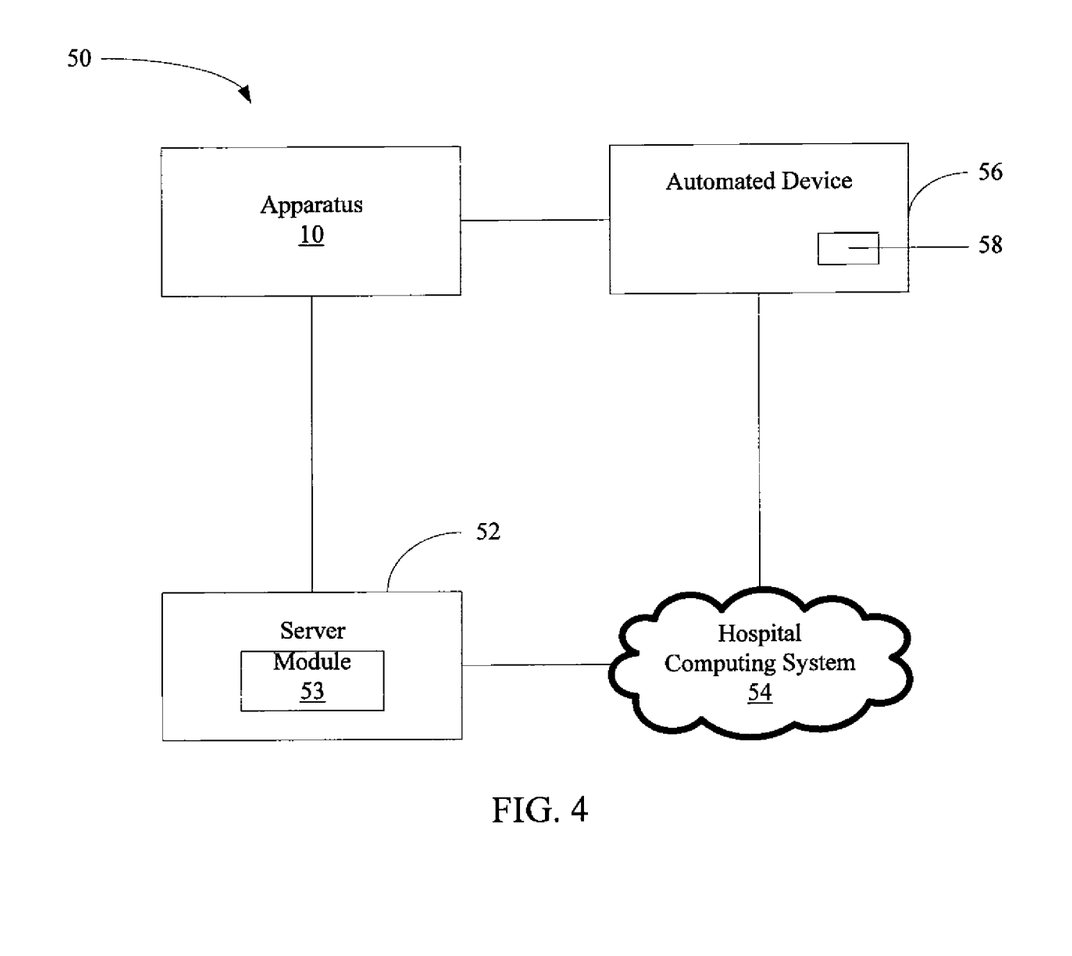
FIG. 4 illustrates various embodiments of a system which includes the apparatus of FIG. 1.

FIG. 4 illustrates various embodiments of a system 50 which includes the apparatus 10 of FIG. 1. The system 50 includes a server 52 is in wireless communication with the apparatus 10. The server 52 may receive data transmitted from the apparatus 10, and such data may indicate the position of the apparatus 10 within the facility, a log of who gained access to the items in the secure storage areas 34 of the cart 14, a log of the items removed from the secure storage areas 34 of the cart 14, a log of the access and removal times, etc. The server 52 includes a module 53 configured to maintain a chain of custody record for each item securely transported by the apparatus 10. The module 53 may be implemented in hardware, firmware, software and combinations thereof. For embodiments utilizing software, the software may utilize any suitable computer language (e.g., C, C++, Java, JavaScript, Visual Basic, VB Script, Delphi) and may be embodied permanently or temporarily in any type of machine, component, physical or virtual equipment, storage medium, or propagated signal capable of delivering instructions to a device. The module 53 (e.g., software application, computer program) may be stored on a computer-readable medium (e.g., disk, device, and/or propagated signal) such that when a computer reads the medium, the functions described herein are performed.

The server 52 may also be in communication with a hospital computing system 54 which is in communication with one or more automated devices (e.g., ADCs) 56 positioned throughout the facility. For purposes of simplicity, the automated devices 56 will be described in the context of ADCs. The ADCs 56 may be similar to those described hereinabove, and may also include a receiver 58 for receiving the instructions communicated from the apparatus 10. The receiver 58 is in communication with a computing device of the ADC, and the computing device is operative to unlock one or more of the drawers of the ADC based on the instructions transmitted by the apparatus 10 and/or inputs entered by a hospital employee.

Figure 5:
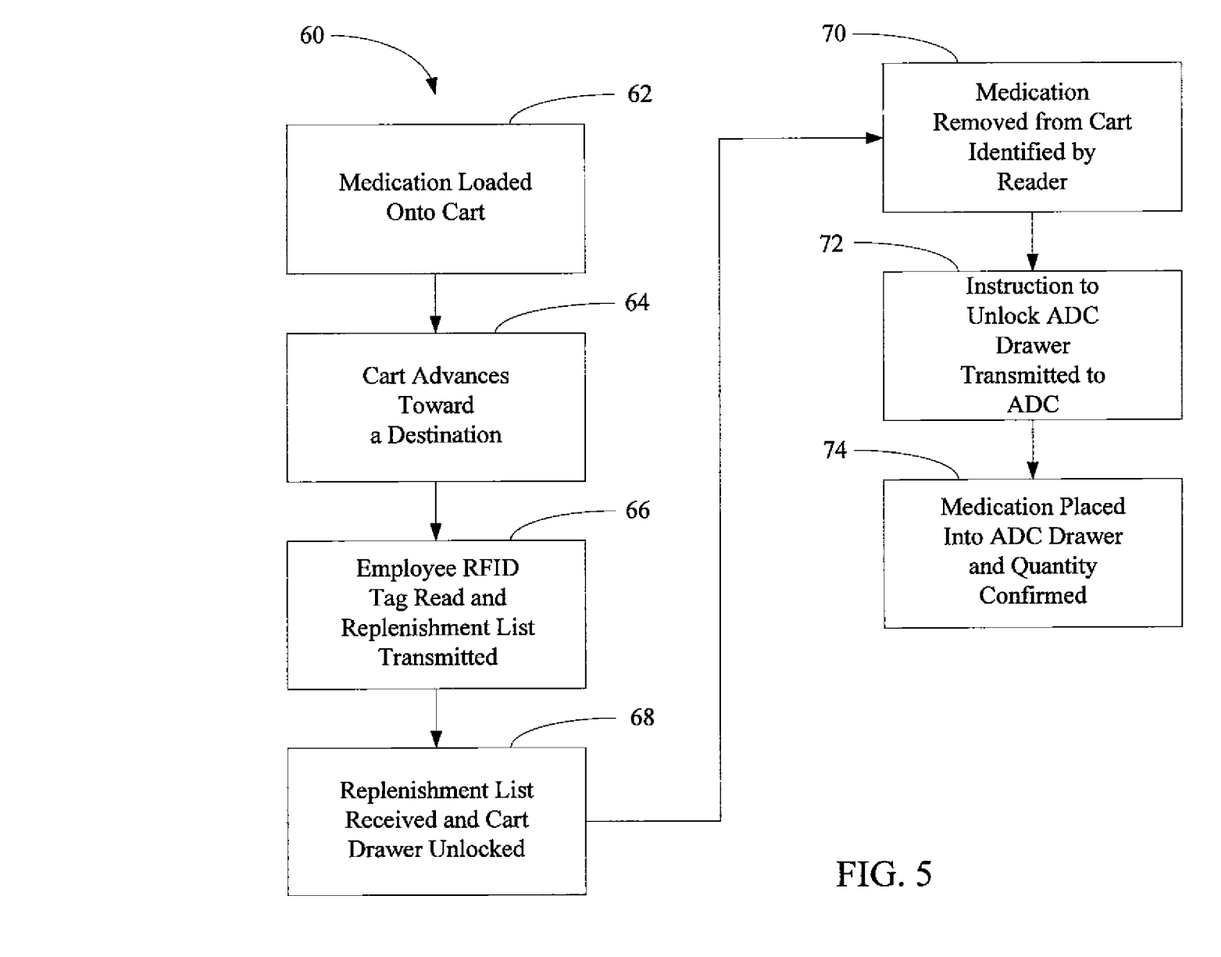
FIG. 5 illustrates various embodiments of a method for transporting an item.

FIG. 5 illustrates various embodiments of a method 60 for securely transporting items within an environment. The items may include for example, medicines, lab specimens, blood products, food, general supplies, mail, etc. For purposes of simplicity, the method 60 will be described in the context of delivering medications from a hospital pharmacy to one or more automated dispensing cabinets positioned throughout a hospital facility. The method 60 may be implemented by the apparatus 10 of FIG. 1. When utilized with the system 50 of FIG. 4, the method 60 provides positive identification and automatic chain of custody records regarding the transfer of items from one location to another location (e.g., from the hospital pharmacy to various ADCs positioned throughout the hospital facility).

Prior to the start of the process 60, the respective ADCs 56 communicate information back to the hospital computing system 54 regarding which medication packages have been removed from the ADCs 56. Therefore, at any given point in time, the hospital computing system 54 knows the type and amount of medication packages which need to be replenished at the respective ADCs 56.

The process starts at block 62, where medication packages needed to replenish the ADCs 56 are loaded into the cart 14 at the hospital pharmacy. The RFID tag of the person loading the cart 14 is read by the first passive RFID tag reader 38, and the second passive RFID tag reader 40 and/or the bar code reader 42 are utilized to read each medication package as the packages are loaded into the cart 14, thereby capturing the beginning information for the chain of custody record. Alternatively, the person may subject a part of their body (e.g., a thumb) to a biometric reader to allow for identification of the person who loads the medication packages into the cart 14.

Once the cart 14 is loaded and locked, the process advances from block 62 to block 64, where the apparatus 10, including the loaded cart 14, advances toward a first one of the ADCs 56 positioned throughout the patient areas of the hospital facility. For embodiments where the apparatus 10 includes the mobile robot 12, the apparatus advances autonomously toward the first one of the ADCs 56. Otherwise, the cart 14 is manually pushed or pulled toward the first one of the ADCs 56. While the apparatus 10 is traveling to the first ADC 56, the apparatus 10 may communicate continually or intermittently with the server 52.

Upon its arrival at the first ADC 56, the process advances from block 64 to block 66, where a hospital employee approaches the apparatus 10 so that the hospital issued passive RFID tag of that employee is read by the first passive RFID reader 38 of the cart 14. If the employee is authorized to access the cart 14 and the ADC 56, the interface 16 transmits an instruction to the ADC 56 to display a list of medication packages which need to be replenished at the ADC 56. Alternatively, the authorization process may require the hospital employee to subject a body part (e.g., a thumb) to a biometric reader in lieu of or in addition to the reading of the hospital issued passive RFID tag of the employee.

From block 66, the process advances to block 68, where the interface 16 receives the list from the ADC 56, and operates to unlock the secure storage area 34 which holds the first medication package on the list, thereby providing the authorized hospital employee access to the needed medication package. At this point, the apparatus 10 may transmit information to the server 54 regarding the identity of the employee, the time the employee was authenticated, etc.

From block 68, the process advances to block 70, where the authorized hospital employee removes one or more of the first medication packages from the list from the cart 14. Upon removal of the one or more first medication packages from the cart 14, the second passive RFID tag reader 40 identifies each removed medication package. If the cart 14 is equipped with the bar code reader 42 in lieu of the second passive RFID reader 40, the employee may utilize the bar code reader 42 to read the bar code on each of the removed medication packages. The apparatus 10 may transmit the removal information to the server 54.

From block 70, the process advances to block 72, where the interface 16 transmits an instruction to the ADC 56 to unlock a drawer of the ADC 56 associated with the one or more of the first medication packages which were removed from the cart 14. By unlocking the correct drawer of the ADC 56 based on the identification of the one or more of the first medication packages removed from the cart 14, the need for the authorized hospital employee to enter the drawer code is eliminated, thereby saving time and increasing the accuracy of the restocking process.

After the one or more of the first medication packages are placed into the drawer of the ADC 56, the process advances to block 74, where the authorized employee confirms the quantity of the medication packages added to the ADC 56, and the drawer is closed and locked. The ADC 56 communicates the quantity information to the interface 16, thereby adding to the chain of custody information for that particular medication package. The ADC 56 may also transmit the quantity information to the hospital computing system 54.

After block 74, the apparatus 10 advances toward a second one of the ADCs 56 positioned throughout the patient areas of the hospital facility. Upon arrival at the second ADC 56, the process may advance in a manner similar to that described hereinabove with respect to blocks 66-74. The process may be repeated any number of times for any number of ADCs.

Nothing in the above description is meant to limit the invention to any specific materials, geometry, or orientation of elements. Many part/orientation substitutions are contemplated within the scope of the invention and will be apparent to those skilled in the art. The embodiments described herein were presented by way of example only and should not be used to limit the scope of the invention.

Although the invention has been described in terms of particular embodiments in this application, one of ordinary skill in the art, in light of the teachings herein, can generate additional embodiments and modifications without departing from the spirit of, or exceeding the scope of, the described invention. For example, in lieu of securely transporting a medicine within a hospital, the invention may be utilized to securely transport some other item in some other environment. Accordingly, it is understood that the drawings and the descriptions herein are proffered only to facilitate comprehension of the invention and should not be construed to limit the scope thereof.

What is claimed is:

1. A system, comprising:
an apparatus configured for securely transporting an item from a first location within a facility to a second location within the facility, the apparatus comprising:
a mobile robot; and
a cart coupled to the mobile robot, wherein:
the cart comprises:
a biometric reader; and
at least one secure storage area having the item stored therein;
the cart is configured to automatically unlock the at least one secure storage area; and
the mobile robot is configured to autonomously advance the cart from the first location to the second location; and
a server communicably connected to the apparatus, wherein the server is configured for:
receiving information transmitted from the apparatus, wherein the received information comprises:
information associated with a person who loaded the item into the at least one secure storage area at the first location;
information associated with a position of the cart within the facility; and
information associated with a person who removed the item from the at least one secure storage area at the second location; and
generating and maintaining a chain of custody record for the item based on the received information, wherein the chain of custody record comprises:
the information associated with a person who loaded the item into the at least one secure storage area at the first location;
the information associated with the position of the cart within the facility; and
the information associated with a person who removed the item from the at least one secure storage area at the second location.

2. The system of claim 1, wherein the mobile robot comprises a computing device.

3. The system of claim 2, wherein the mobile robot further comprises a plurality of sensors connected to the computing device.

4. The system of claim 2, wherein the mobile robot further comprises a power source connected to the computing device.

5. The system of claim 4, wherein the computing device further comprises a motor connected to the battery.

6. The system of claim 1, wherein the cart further comprises an input device.

7. The system of claim 1, wherein the cart further comprises a radio-frequency identification tag reader.

8. The system of claim 1, wherein the cart further comprises a bar code reader.

9. The system of claim 1, wherein the cart is electrically and mechanically coupled to the mobile robot.

10. The system of claim 1, wherein the apparatus further comprises a post configured to couple the mobile robot with the cart.

11. The system of claim 10, wherein the mobile robot defines a receptacle configured for receiving the post.

12. The system of claim 1, further comprising an interface connected to the cart, wherein the interface is configured to wirelessly communicate with at least one other automated device.

13. A method for securely transporting an item, the method comprising:
   identifying an item placed into a secured storage area of a cart at a first location within a facility;
   utilizing a biometric reader to identify a person who placed the item into the secured storage area of the cart;
   transmitting placement information regarding the identified item to a server;
   autonomously advancing the cart from the first location to a second location within the facility;
   transmitting information regarding a position of the cart within the facility to the server;
   automatically unlocking the secured storage area of the cart at the second location;
   identifying the item when it is removed from the secured storage area of the cart at the second location; and
   transmitting removal information regarding the identified item to the server.

14. The method of claim 13, wherein identifying the item comprises identifying the item with a radio-frequency identification tag reader.

15. The method of claim 13, wherein identifying the item comprises identifying the item with a bar code reader.

16. The method of claim 13, further comprising maintaining a chain of custody record associated with the item.

* * * * *